United States Patent [19]

Jimonet et al.

[11] Patent Number: 5,068,238
[45] Date of Patent: Nov. 26, 1991

[54] 2-ALKYLIMINOBENZOTHIAZOLINE DERIVATIVES, PROCESSES FOR PREPARING THEM AND MEDICINAL PRODUCTS CONTAINING THEM

[75] Inventors: Patrick Jimonet, Villepreux; Conception Nemecek, Choisy le Roi, both of France

[73] Assignee: Rhone-Poulenc Sante, Antony Cedex, France

[21] Appl. No.: 545,822

[22] Filed: Jun. 29, 1990

[30]. * Foreign Application Priority Data

Jul. 13, 1989 [FR] France .................. 89 09481

[51] Int. Cl.$^5$ .................. C07D 277/82; A61K 31/425
[52] U.S. Cl. .................. 514/367; 548/161
[58] Field of Search .................. 548/161, 164; 514/367

[56] References Cited

U.S. PATENT DOCUMENTS

| 4,370,338 | 1/1983 | Mizoale | 548/164 |
| 4,980,536 | 12/1990 | Audiau | 548/161 |
| 5,008,280 | 4/1991 | Gueremy | 548/161 |

FOREIGN PATENT DOCUMENTS

| 50551 | 4/1982 | European Pat. Off. | 548/161 |
| 667091 | 9/1988 | Switzerland | 548/161 |

OTHER PUBLICATIONS

Metzger, Thiazoles, vol. 2, pp. 32-34 (1979).
Mar., Advanced Org. Reactions, 3rd ed., pp. 1089-1090 (1985).
European Search Report dated Feb. 27, 1990.

*Primary Examiner*—Robert Gerstl
*Attorney, Agent, or Firm*—Morgan & Finnegan

[57] ABSTRACT

Compounds of formula:

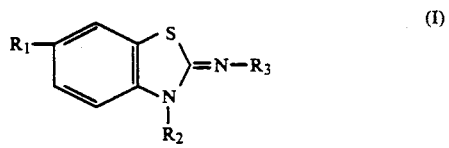

$R_1$ represents a polyfluoroalkoxy radical,
$R_2$ represents an alkylthioalkyl, alkylsulphinylalkyl or alkylsulphonylalkyl radical, and
$R_3$ represents an alkyl radical, as well as the salts of these compounds with an inorganic or organic acid, processes for preparing them and medicinal products containing them.

4 Claims, No Drawings

2-ALKYLIMINOBENZOTHIAZOLINE DERIVATIVES, PROCESSES FOR PREPARING THEM AND MEDICINAL PRODUCTS CONTAINING THEM

FIELD OF THE INVENTION

The present invention relates to 2-alkyliminobenzothiazoline derivatives of formula:

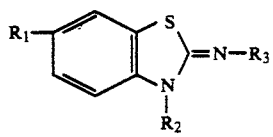

to their salts, to processes for preparing them and to medicinal products containing them.

In the formula (I), $R_1$ represents a polyfluoroalkoxy radical, $R_2$ represents an alkylthioalkyl, alkylsulphinylalkyl or alkylsulphonylalkyl radical, and $R_3$ represents an alkyl radical.

In the definitions above and those to be mentioned below, the alkyl radicals and alkyl and alkoxy portions contain 1 to 4 carbon atoms in a straight or branched chain.

The polyfluoroalkoxy radicals are preferably trifluoromethoxy, pentafluoroethoxy, 2,2,2-trifluoroethoxy or 1,1,2,2-tetrafluoroethoxy radicals.

The invention also relates to the addition salts of the compounds of formula (I) with inorganic or organic acids.

DETAILED DESCRIPTION OF THE INVENTION

According to the invention, the compounds of formula (I) may be prepared by the action of a derivative of formula:

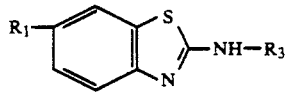

in which $R_1$ and $R_3$ have the same meanings as in the formula (I), on a derivative of formula:

$$R_2-X \quad (III)$$

in which $R_2$ has the same meanings as in the formula (I) and X represents a reactive group such as a tosyloxy radical or a halogen atom (preferably chlorine, bromine or iodine), or an addition salt of such a derivative with an inorganic or organic acid.

This reaction is generally performed in an inert organic solvent such as an alcohol (ethanol, propanol, etc.), a ketone (acetone, methyl ethyl ketone, etc.) or dimethylformamide, at a temperature between 20° C. and the boiling point of the solvent, optionally in the presence of sodium iodide.

The derivatives of formula (II) may be obtained by the action of an alkylamine on a 2-chloro-6-polyfluoroalkoxybenzothiazole.

This reaction is preferably performed in an aqueous medium.

2-Chloro-6-polyfluoroalkoxybenzothiazoles may be obtained by the chlorination of a 2-hydrazino-6-polyfluoroalkoxybenzothiazole.

The chlorination is performed by means of a chlorinating agent, preferably by means of thionyl chloride, at a temperature of between 20° C. and 70° C.

2-Hydrazino-6-polyfluoroalkoxybenzothiazoles may be prepared by the action of hydrazine on a 2-amino-6-polyfluoroalkoxybenzothiazole.

This reaction is generally performed in an organic solvent such as ethylene glycol, at a temperature in the region of 140° C.

2-Amino-6-polyfluoroalkoxybenzothiazoles may be obtained by application or adaptation of the method described by L. M. YAGUPOL'SKII et al., Zh. Obshch. Khim. 33 (7), 2301 (1963).

The compounds of formula (I) for which $R_2$ represents an alkylsulphinylalkyl or alkyl-sulphonyl-alkyl radical may also be obtained by oxidation of the corresponding derivatives of formula (I) for which $R_2$ represents an alkylthioalkyl radical.

The oxidation to alkylsulphinylalkyl is generally performed by means of m-chloroperbenzoic acid, in an alcohol, at a temperature of between $-15°$ C. and $-40°$ C.

The oxidation to alkylsulphonylalkyl may be performed by means of hydrogen peroxide, in acetic acid, at a temperature in the region of 100° C., or by means of m-chloroperbenzoic acid in an inert solvent such as dichloromethane or chloroform, at a temperature in the region of 20° C.

The reaction mixtures obtained by the various processes described above are treated according to conventional physical methods (evaporation, extraction, distillation, crystallization, chromatography, etc.) or chemical methods (salt formation, etc.).

The compounds of formula (I), in free base form, can be optionally converted to addition salts with an inorganic or organic acid, by the action of such an acid in an organic solvent such as an alcohol, ketone, ether or chlorinated solvent.

The compounds of formula (I) and their salts possess advantageous pharmacological properties. These compounds are active with respect to glutamate-induced convulsions, and are hence useful in the treatment and prevention of convulsive phenomena, schizophrenic disorders, and in particular the deficiency forms of schizophrenia, sleep disorders, phenomena linked to cerebral ischaemia and also neurological conditions in which glutamate may be implicated, such as Alzheimer's disease, Huntington's chorea, amyotrophic lateral sclerosis and olivopontocerebellar atrophy.

The activity of the compounds of formula (I), with respect to glutamate-induced convulsions was determined according to a technique based on that of I.P. LAPIN, J. Neural. Transmission, vol. 54, 229–238 (1982); intracerebroventricular injection of glutamate being performed according to a technique based on that of R. CHERMAT and P. SIMON, J. Pharmacol. (Paris), vol. 6, 489–492 (1975). Their ED$_{50}$ is less than 10 mg/kg.

The compounds of formula (I) possess low toxicity. Their LD$_{50}$ is more than 15 mg/kg when administered I.P. in mice.

For medicinal use, the compounds of formula (I) may be employed as they are, or in the state of pharmaceutically acceptable salts, i.e. salts which are non-toxic at the doses at which they are used.

As examples of pharmaceutically acceptable salts, the addition salts with inorganic or organic acids, such as acetate, propionate, succinate, benzoate, fumarate, maleate, oxalate, methanesulphonate, isethionate, theophyllineacetate, salicylate, phenolphthalinate, methylenebis(β-hydroxynaphthoate), hydrochloride, sulphate, nitrate and phosphate, may be mentioned.

EXAMPLES

The examples which follow, given without implied limitation, show how the invention may be put into practice.

EXAMPLE 1

A mixture of 2-methylamino-6-trifluoromethoxybenzothiazole (12.4 g) and 1-chloro-2-methylthioethane (6.6 g) in methyl ethyl ketone (75 cc) is heated to boiling for 72 hours. After cooling to a temperature in the region of 20° C., the precipitate formed is filtered off and washed with ethyl ether (3×50 cc). 2-Methylimino-3-(2-methylthioethyl)-6-trifluoro-methoxybenzothiazoline hydrochloride (5.7 g), subliming at about 210° C., is obtained.

2-Methylamino-6-trifluoromethoxybenzothiazole may be prepared according to the following process: 2-chloro-6-trifluoromethoxybenzothiazole (22.0 g) and 40% strength aqueous methylamine (90 cc) are heated in an autoclave at 110° C. for 24 hours. After cooling to a temperature in the region of 20° C., the reaction medium is added to distilled water (300 cc) and the precipitate formed filtered off and washed with distilled water (2×100 cc). After drying, 2-methylamino-6-trifluoromethoxybenzothiazole (19.5 g), m.p. 162° C., is obtained.

2-Chloro-6-trifluoromethoxybenzothiazole may be prepared in the following manner: 2-hydrazino-6-trifluoromethoxybenzothiazole (133 g) is added in the course of 1 hour and a half to thionyl chloride (162 cc) heated to 50° C. Reaction is continued for 1 hour at this temperature. After cooling to a temperature in the region of 20° C., the reaction medium is poured into ice-cold water (2.5 liters). The precipitate formed is filtered off, washed with distilled water (2 liters) and then taken up in dichloromethane (1 liter). The organic phase is washed with distilled water (3×200 cc), then dried over magnesium sulphate and concentrated to dryness under reduced pressure (20 mm Hg; 2.7 kPa). 2-Chloro-6-trifluoromethoxybenzothiazole (122.4 g), m.p. below 50° C., is obtained.

2-Hydrazino-6-trifluoromethoxybenzothiazole may be prepared according to the following process: a mixture of 2-amino-6-trifluoromethoxybenzothiazole (140.4 g), 85% strength hydrazine hydrate (69.6 cc) and hydrazine dihydrochloride (63 g) in ethylene glycol (600 cc) is heated to 140° C. for 2 hours under a stream of nitrogen. After cooling to a temperature in the region of 20° C., the precipitate formed is filtered off and washed with distilled water (4×250 cc) and then with ethyl ether (100 cc). 2-Hydrazino-6-trifluoromethoxybenzothiazole (133.0 g), m.p. 208° C., is obtained.

2-Amino-6-trifluoromethoxybenzothiazole may be prepared according to the method described by L. M. YAGUPOL'SKII et al., Zh. Obshch. Khim., 33 (7), 2301 (1963).

EXAMPLE 2

The procedure is as in Example 1, starting with 2-methylamino-6-trifluoromethoxybenzothiazole (7.1 g) and 1-chloro-2-ethylthioethane (4.2 g) in methyl ethyl ketone (10 cc). After 48 hours at the boil, the reaction medium is cooled to a temperature in the region of 20° C. The precipitate formed is filtered off and washed with methyl ethyl ketone (3×10 cc). After recrystallization in 2-propanol (50 cc), 2-methylimino-3-(2-ethylthioethyl)-6-trifluoromethoxybenzothiazoline hydrochloride (5.3 g), subliming at about 150° C., is obtained.

EXAMPLE 3 m-Chloroperbenzoic acid (2.0 g) is added in the course of approximately 10 minutes to 2-methylimino-3-(2-methylthioethyl)-6-trifluoromethoxybenzothiazoline (2.6 g) dissolved in absolute ethanol (40 cc) cooled to −30° C. Reaction is continued for 15 minutes at the same temperature. The reaction medium is then diluted with ethyl ether (100 cc) and treated with 4.2N ethereal ether hydrogen chloride (2.2 cc). The precipitate formed is filtered off and then recrystallized in 2-propanol (30 cc). (RS)-2-Methylimino-3-(2-methylsulphinylethyl-)-6-trifluoromethoxybenzothiazoline hydrochloride (2.0 g), subliming at about 170° C., is obtained.

EXAMPLE 4 m-Chloroperbenzoic acid (2.5 g) is added in the course of approximately 10 minutes to 2-methylimino-3-(2-ethylthioethyl)-6-trifluoromethoxy-benzothiazoline (3.7 g) dissolved in absolute ethanol (50 cc) cooled to −20° C. Reaction is continued for 15 minutes at the same temperature. The reaction medium is then diluted with ethyl ether (100 cc) and treated with 4.2N ethereal hydrogen chloride (2.5 cc). The precipitate formed is filtered off, then taken up in distilled water (50 cc) and neutralized with 1N sodium hydroxide. After extraction with ethyl acetate, drying over magnesium sulphate and concentration to dryness under reduced pressure (20 mm Hg; 2.7 kPa), the crude product is purified by chromatography on a silica column, with ethyl acetate and then a mixture of ethyl acetate and methanol (80:20 by volume) as eluents. After conversion to hydrochlorides, 2-methylimino-3-(2-ethylsulphonylethyl)-6-trifluoromethoxybenzothiazoline hydrochloride (0.5 g), subliming at about 180° C., and (RS)-2-methylimino-3-(2-ethylsulphinylethyl)-6-trifluoromethoxybenzothiazoline (1.9 g), subliming at about 180° C., are obtained.

EXAMPLE 5

A mixture of 2-ethylamino-6-trifluoromethoxybenzothiazole (7.45 g) and 1-chloro-2-methylthioethane (3.76 g) in methyl ethyl ketone (20 cc) is heated to boiling for 94 hours. After cooling to a temperature in the region of 20° C., the precipitate formed is filtered off and washed with methyl ethyl ketone (2×20 cc). After recrystallization in 2-propanol, 2-ethylimino-3-(2-methylthioethyl)-6-trifluoromethoxybenzothiazoline hydrochloride (0.75 g), m.p. 208° C., is obtained.

2-Ethylamino-6-trifluoromethoxybenzothiazole may be prepared according to the following process: 2-chloro-6-trifluoromethoxybenzothiazole (11 g) and 33% strength aqueous ethylamine (80 cc) are heated in an autoclave at 110° C. for 24 hours. After cooling to a temperature in the region of 20° C., the reaction medium is added to distilled water (200 cc) and the precipitate formed is filtered off and washed with distilled water (2×100 cc). 2-Ethylamino-6-trifluoromethoxybenzothiazole (10.32 g), m.p. 135° C., is obtained.

The present invention also relates to medicinal products consisting of at least one compound of formula (I), or a salt of such a compound, in the pure state or in the form of a composition in which it is combined with any other pharmaceutically compatible product, which can be inert or physiologically active. The medicinal products according to the invention may be employed orally, parenterally, rectally or topically.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica.

These compositions can also comprise substances other than diluents, e.g. one or more lubricants such as magnesium stearate or talc, a coloring, a coating (dragées) or a varnish.

As liquid compositions for oral administration, solutions, suspensions, emulsions, syrups and elixirs of a pharmaceutically acceptable nature, containing inert diluents such as water, ethanol, glycerol, vegetable oils or liquid paraffin, may be used. These compositions can comprise substances other than diluents, e.g. wetting products, sweeteners, thickeners, flavorings or stabilizers.

The sterile compositions for parenteral administration can preferably be suspensions, emulsions or non-aqueous solutions. As a solvent or vehicle, water, propylene glycol, a polyethylene glycol, vegetable oils, especially olive oil, injectable organic esters, e.g. ethyl oleate, or other suitable organic solvents may be employed. These compositions can also contain adjuvants, especially wetting agents, tonicity regulators, emulsifiers, dispersants and stabilizers. The sterilization may be carried out in several ways, e.g. by aseptic filtration, by incorporating sterilizing agents in the composition, by irradiation or by heating. They may also be prepared in the form of sterile solid compositions which can be dissolved at the time of use in sterile water or any other sterile injectable medium.

The compounds for rectal administration are suppositories or rectal capsules which contain, apart from the active product, excipients such as cocoa butter, semisynthetic glycerides or polyethylene glycols.

The compounds for topical administration can be e.g. creams, ointments, lotions, eye washes, mouth washes, nasal drops or aerosols.

In human therapy, the compounds according to the invention are especially useful in the treatment and prevention of convulsive phenomena, schizophrenic disorders, and in particular the deficiency forms of schizophrenia, sleep disorders, phenomena linked to cerebral ischaemia and neurological conditions in which glutamate may be implicated, such as Alzheimer's disease, Huntington's chorea, amyotrophic lateral sclerosis and olivopontocerebellar atrophy.

The doses depend on the effect sought, the treatment period and the administration route used; they are generally between 30 and 300 mg per day in oral administration for an adult, with unit doses ranging from 10 to 100 mg of active substance.

Generally speaking, the doctor will determine the appropriate dosage in accordance with the age and weight and all other factors characteristic of the subject to be treated.

EXAMPLES

The examples which follow illustrate compositions according to the invention:

EXAMPLE A

Hard gelatin capsules containing 50 mg of active product and having the following composition are prepared according to the usual technique:

| | |
|---|---|
| 2-methylimino-3-(2-methylthioethyl)-6-trifluoromethoxybenzothiazoline | 50 mg |
| cellulose | 18 mg |
| lactose | 55 mg |
| colloidal silica | 1 mg |
| carboxymethylstarch sodium | 10 mg |
| talc | 10 mg |
| magnesium stearate | 1 mg |

EXAMPLE B

Tablets containing 50 mg of active product and having the following composition are prepared according to the usual technique:

| | |
|---|---|
| 2-methylimino-3-(2-ethylthioethyl)-6-trifluoromethoxybenzothiazoline | 50 mg |
| lactose | 104 mg |
| cellulose | 40 mg |
| polyvidone | 10 mg |
| carboxymethylstarch sodium | 22 mg |
| talc | 10 mg |
| magnesium stearate | 2 mg |
| colloidal silica | 2 mg |
| mixture of hydroxymethyl cellulose, glycerol and titanium oxide (72:3.5:24.5) q.s. | 1 finished |
| tablet weighing | 245 mg |

EXAMPLE C

An injectable solution containing 10 mg of active product and having the following composition is prepared:

| | |
|---|---|
| 2-methylimino-3-(2-ethylsulphonylethyl)-6-trifluoromethoxybenzothiazoline | 10 mg |
| benzoic acid | 80 mg |
| benzyl alcohol | 0.06 cc |
| sodium benzoate | 80 mg |
| ethanol, 95% | 0.4 cc |
| sodium hydroxide | 24 mg |
| propylene glycol | 1.6 cc |
| water q.s. | 4 cc |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A compound of formula:

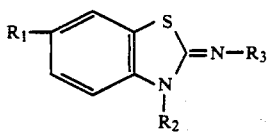 (I)

in which
- R₁ represents a polyfluoroalkoxy radical,
- R₂ represents an alkylthioalkyl, alkylsulphinylalkyl or alkylsulphonylalkyl radical, and
- R₃ represents an alkyl radical, on the understanding that the alkyl radicals and alkyl and alkoxy portions contain 1 to 4 carbon atoms in a straight or branched chain, as well as its addition salts with an inorganic or organic acid.

2. The compound according to claim 1 for which R₁ represents a trifluoromethoxy, pentafluoroethoxy, 2,2,2-trifluoroethoxy or 1,1,2,2-tetrafluoroethoxy radical.

3. A pharmaceutical composition comprising, as active ingredient, at least one compound according to claim 1 or a pharmaceutically acceptable salt of such compound in association with a pharmaceutically acceptable carrier.

4. A method for the treatment of a medical condition associated with the effects of glutamate comprising administering to a subject in need of such treatment an amount of a compound according to claim 1 or a pharmaceutically acceptable salt of such a compound, sufficient to inhibit such effects.

* * * * *